United States Patent
Su et al.

(10) Patent No.: US 9,446,018 B2
(45) Date of Patent: Sep. 20, 2016

(54) PHARMACEUTICAL COMPOSITION FOR TREATING OR PREVENTING ANGINA OR MYOCARDIAL INFARCTION INDUCED BY MYOCARDIAL ISCHEMIA

(75) Inventors: Muh-Hwan Su, I Lan (TW); Jing Jing Justine Tang, I Lan (TW); Hang-Ching Lin, Taipei (TW)

(73) Assignee: SINPHAR TIAN-LI PHARMACEUTICAL CO., LTD. (HANGZHOU), Zheijiang (CN)

( * ) Notice: Subject to any disclaimer, the term of this patent is extended or adjusted under 35 U.S.C. 154(b) by 0 days.

(21) Appl. No.: 13/383,261

(22) PCT Filed: Jul. 10, 2009

(86) PCT No.: PCT/CN2009/000788
§ 371 (c)(1),
(2), (4) Date: Jan. 10, 2012

(87) PCT Pub. No.: WO2011/003223
PCT Pub. Date: Jan. 13, 2011

(65) Prior Publication Data
US 2012/0232041 A1 Sep. 13, 2012

(51) Int. Cl.
| *A61K 31/353* | (2006.01) |
| *A61K 31/616* | (2006.01) |
| *A61P 9/10* | (2006.01) |
| *A61K 36/539* | (2006.01) |
| *A61K 36/185* | (2006.01) |
| *A61K 36/82* | (2006.01) |
| *A61K 45/06* | (2006.01) |

(52) U.S. Cl.
CPC ............. *A61K 31/353* (2013.01); *A61K 36/82* (2013.01); *A61K 45/06* (2013.01)

(58) Field of Classification Search
CPC ...... A61K 31/353; A61K 36/82; A61K 45/06
USPC .......................... 514/161, 456; 424/725, 729
See application file for complete search history.

(56) References Cited

U.S. PATENT DOCUMENTS

2006/0204596 A1 * 9/2006 Jia et al. .................... 424/725
2008/0161296 A1 * 7/2008 Davis et al. .............. 514/223.5

FOREIGN PATENT DOCUMENTS

| JP | 59025322 A | * | 2/1984 | ............. A61K 31/34 |
| JP | 2004315379 A | * | 11/2004 | ............... A23L 1/30 |
| WO | 0021507 A2 | | 4/2000 | |

OTHER PUBLICATIONS

USDA Database for the Flavonoid Content of Selected Foods: retrieved from internet: home.ix.netcom.com/~jdalton/flav.pdf. Retrieved on Sep. 17, 2013.*

(Continued)

*Primary Examiner* — Ernst V Arnold
*Assistant Examiner* — Hong Yu
(74) *Attorney, Agent, or Firm* — Bacon & Thomas, PLLC (57) ABSTRACT

The present invention provides a pharmaceutical composition for the treatment and prophylaxis of angina and myocardial infarction, wherein a combination of a tea extract (catechins) and an antianginal drug are proved therapeutically potent in treating angina and myocardial infarction induced from myocardial ischemia. The present invention also provides a use of a tea extract (catechins) in treating and preventing angina.

8 Claims, 3 Drawing Sheets

(56) References Cited

OTHER PUBLICATIONS

Phenolic content in tea: retrieved from internet: http://en.wikipedia.org/wiki/Phenolic_content_in_tea. Retrived on Sep. 18, 2013.*
Green Tea Extract (Decaffeinated): retrieved from internet: http://www.naturalhealthyconcepts.com/green-tea-extract-p-pure-encapsulations.html?gclid=CKqkw-Pr0rkCFRGi4AodhHwAIQ. Retrieved on Sep. 18, 2013.*
Nebivolol: retrieved from internet: http://en.wikipedia.org/wiki/Nebivolol. Retrieved on Jun. 18, 2014.*
Green tea extract: retrieved from internet: http://en.wikipedia.org/wiki/Green_tea_extract. Retrieved on Jan. 5, 2015.*
Shen et al.: Determination of the predominant catechins in Acacia catechu by Liquid Chromatography/Electrospray ionization-Mass Spectrometry, Journal of Agriculture and Food Chemistry, 2006, 54, 3219-3229.*
Zwaan et al.: Mechanisms of cell death in acute myocardial infarction: pathophysiological implications for treatment, Netherlands Heart Journal, vol. 9, No. 1, 2001.*
Jiao Shilan, et al. Tea polyphenols on the improvement of clinical symptoms in patients with coronary heart disease. Practical Journal of Medicine & Pharmacy, Jan. 2006, vol. 23, No. 1, pp. 54-55, ISSN: 1671-4008. (See Written Opinion to PCT/CN2009/000788 dated Apr. 15, 2010.
Liang Tiejun et al. Effect of tibao xinnaojian tablets on platelet mobilizing function in patients with unstable angina pectoris. Journal of Emergency Medicine, Oct. 1999, vol. 8, No. 5, pp. 343-344, ISSN: 1006-463X. (See Written Opinion to PCT/CN2009/000788 dated Apr. 15, 2010).
Li Yanwei et al. Observation on curative effect of xinkang capsule for unstable effort angina. China Journal of Basic Medicine in Traditional Chinese Medicine, 2004, vol. 10, No. 3, pp. 67-69, ISSN: 1006-3250. (See Written Opinion to PCT/CN2009/000788 dated Apr. 15, 2010).
Lin Hong. Tea polyphenols' pharmacological effect on the cardiovascular system. Tianjin Pharmacy, May 1999, vol. 11, No. 2, pp. 11-12, ISSN: 1006-5687. (See Written Opinion to PCT/CN2009/000788 dated Apr. 15, 2010).
Dia Qian et al. Progress in the treatment of unstable angina pectoris. Chinese Journal of Difficult and Complicated Cases, Aug. 2007, vol. 6, No. 8, pp. 505-508. (See Written Opinion to PCT/CN2009/000788 dated Apr. 15, 2010).
Zeng Bin et al. Myocardial Infarction and Drug Treatment, China Practical Medicine, Jun. 2008, vol. 3, No. 16, pp. 88-89. (See Written Opinion to PCT/CN2009/000788 dated Apr. 15, 2010).
PCT International Preliminary Report on Patentability for PCT/CN2009/000788 dated Apr. 15, 2010.

* cited by examiner

PHARMACEUTICAL COMPOSITION FOR TREATING OR PREVENTING ANGINA OR MYOCARDIAL INFARCTION INDUCED BY MYOCARDIAL ISCHEMIA

FIELD OF THE INVENTION

The present invention relates to prophylaxis and treatment of cardiac damage, angina, and myocardial infarction induced from myocardial ischemia.

BACKGROUND OF THE INVENTION

Cardiac contractions (i.e. cardiac work) play a vital role in pumping blood from the heart to the organs, tissues, and cells in the human body, and are driven by the coronary artery providing blood (which contains oxygen, glucose, and nutrients mainly) to the myocardial cells. The myocardial cells then consume the oxygen and glucose in order to produce energy (which is ATP) for the heart to carry out further cardiac work. However, the following conditions may hamper blood supplies from reaching the heart properly: (1) when atherosclerosis occurs in the coronary artery and results in the narrowing of the blood vessel; (2) when the coronary artery becomes partially blocked (eg. by the formation of blood clots resulted from platelet aggregation); or (3) when the blood vessel becomes spasmodic and becomes restricted as a result. If the aforesaid conditions are accompanied by increased energy consumption in the human body (eg. during physical exercises), it can lead to insufficient blood supply to the cardiac muscles, which means there is a shortage of blood to the heart, and this in turn can result in angina. If the shortage of blood supply to the coronary artery persists and the cardiac muscles are left without blood for excessively long (from 15 seconds to 15 minutes), it would then lead to death of myocardial cells, which is medically described as myocardial infarction.

When a person experiences angina due to the shortage of blood supply to the cardiac muscles, the person is usually asked to take a rest because reducing cardiac work is the best treatment for angina. With reduced cardiac work, the heart requires less energy consequently, and this means the heart would require less of the substances (oxygen and glucose) needed for producing energy. Therefore, the blood supply from the coronary artery to the cardiac muscles could also be reduced, which relieves angina as a result. The medications used to reduce cardiac work in order to relieve angina can be divided into three types; first of which are nitrates, and second of which are β-blockers, whereas the third are calcium antagonists. The nitrates-based medications reduce cardiac work by: (1) widening the veins so as to keep the blood in the veins, which reduces the blood that circulates back to the heart, and the cardiac work is lowered as the heart does not need to pump as much blood consequently. The venous blood circulation is medically described as the preload, and nitrates are effective for lowering the preload. (2) widening the arteries to reduce the resistance within the blood vessels, such that there is not as much resistance for the heart to pump out the blood. Therefore, the required energy for the cardiac work is lessened as a result. The resistance within the arteries is medically described as the afterload, and nitrates are also effective for lowering the afterload. The β-blockers decrease the cardiac work by reducing the heartbeat, and the consumption of energy could be lowered along with the reduced cardiac work. The calcium antagonists mainly act on the arteries, which prevent calcium from flowing into the cells of the blood vessels, thereby widening the arteries and lowering the resistance within the blood vessels resulted from blood vessel contractions. Therefore, the cardiac work is reduced and the blood can be easily pumped into the organs and the tissues (ie. lowering the afterload).

Angina can be generally divided into three types, which are the stable angina, the unstable angina, and the Prinzmetal's angina. The stable angina is usually resulted from the narrowing of the coronary artery, and can be treated with the aforesaid three types of medication. The unstable angina is the result of fissure in the plaque generated from atherosclerosis of the coronary artery, which not only leads to varying degrees of vessel blockage due to different sizes of platelet aggregation, but also leads to vasospasms as well; both of which subsequently result in reduced blood flows to the coronary artery. This type of angina can also occur while the patient is resting, and the symptoms of which can last longer and be more damaging, and is a foretelling sign of acute myocardial infarction. This type of angina is treated by using the aforesaid three types of medication, in combination with the anti-platelet aggregation drugs, such as Aspirin. The Prinzmetal's angina is less common than the other two types, and is the result of a spasmodic coronary artery. It can be treated by using the calcium antagonists, or by directly widening the coronary artery from using nitrates.

According to past research literature, green tea possesses many chemical components and medicinal properties. Among the chemical components of green tea, tea polyphenols is the term used to describe all polyphenol substances found in tea leaves, which include flavanols, anthocyanins, flavonoids, flavonols, and phenolic acids. The flavanols are the most abundant compounds among the tea polyphenols, they are also called the catechins. In green tea, the main compounds that make up the catechins are catechin (C), epicatechin (EC), epigallocatechin (EGC), epicatechin gallate (ECG), epigallocatechin gallate (EGCG), gallocatechin-3-gallate (GCG), gallocatechin (GC), and catechin-3-gallate (CG).

The catechins occupy approximately 70% of the tea polyphenols in total, and are particularly considered as the main health-promoting component therein. A large number of research literature have shown the medicinal properties thereof, such as: anti-oxidation, anti-inflammation, anti-viral, anti-cancer, anti-atherosclerosis properties, and the ability to reduce weight in test subjects. The relationship between tea and cardiovascular diseases has been extensively studied in the past, which was carried out by using tens of thousands of healthy people from Japan, the Netherlands, and the U.S. as the test subjects, and lasted for six to seven years. The studies had found that drinking tea is closely correlated to lowering the occurrence and risks of cardiovascular and cerebral vessel diseases, and is therefore beneficial to the health of the tea drinkers.

The cardiovascular and cerebral vessel diseases have always been the top three causes of death among the ten most common fatal diseases, and there are approximately 1 million people suffering from myocardial infarction (MI) in the U.S. alone every year.

Myocardial infarction is generally treated by employing thrombolysis, angioplasty, or coronary bypass graft surgery. However, the focus of the present invention is on providing a medication that could delay the death of cardiac muscles when the myocardial cells are dying because of insufficient blood (which is irreversible and called myocardial infarction medically) even though the blood is continuously supplied, or salvage the heart while the cardiac muscles suffer from reversible damage. From the viewpoint of biochemical changes, the death of cardiac muscles is resulted from insufficient blood supply thereto, which in turn leads to insufficient supplies of oxygen and glucose thereto, consequently preventing enough energy (ATP) from being produced in the cardiac muscles and damaging the myocardial cells. Subsequently, the energy insufficiency causes the sodium pumps in the ATP-dependent cell membrane to stop functioning properly, which in turn causes the extracellular sodium, calcium, and water molecules to rush into the cells and make the cells swell up, although the phenomenon is still reversible at this stage. If blood supply is resumed now, the cells could be returned to normal. But if the blood insufficiency continues, the intracellular lysosomes would become lysed, which releases many types of degradation enzymes (such as the degradation enzymes of proteins, lipids, and nucleic acids, etc.) into the intracellular space, along with many kinds of biochemical substances, and the cell membrane are damaged as a result. An important factor that causes the aforesaid catastrophic process is ATP insufficiency, which leads to elevated calcium concentration intracellularly. This is critical because an elevation in calcium concentration actually activates the released enzymes, and further damages the affected cells. Biochemically speaking, the death of cardiac muscles goes through three stages: (1) a shortage of blood leads to ATP insufficiency; (2) the intracellular calcium concentration is elevated subsequently; (3) the lysosomes are released as a result. The damage sustained from up to the second biochemical stage is still reversible. Even though the cells appear to be swelling, the myocardial cells can still be salvaged by supplying oxygen/glucose at this stage. However, the damage sustained from the third biochemical stage is irreversible, and would lead to inevitable death of the cardiac muscles. In the U.S. patent US 2006/0116333 A1, a pharmaceutical composition comprising tea polyphenols for protecting and preserving organs, tissues, or cells has been disclosed, which is applied in a person undergoing an organ transplant operation, so as to protect the person from suffering from organ damage. The damage described in this patent differs from the aforementioned damage caused by partial blood insufficiency in that the heart is still carrying out cardiac work (cardiac contractions) under limited ATP. But when a person undergoes an organ transplant, the heart would have stopped working when it is removed from a human body. Once the heart is transplanted into another human body, it then gives rise to ischemia-reperfusion damage consequently. The ischemia-reperfusion damage occurs because when blood is re-supplied, the oxygen in the blood leads to the production of a new type of enzyme called xanthine oxidase in the cardiac muscles, which is subsequently transformed into harmful free radicals (such as $—O_2^-$, $H_2O_2$, and $—OH$), and damages the cell membrane by peroxidation of lipids therein. In other words, the damage of an organ during an organ transplant is resulted from the generation of free radicals when blood is re-supplied, and the damage can be effectively prevented by providing anti-oxidative substances (which mops up the free radicals). The anti-oxidative substances used in the aforesaid patent are the commonly known tea polyphenols. According to the openly published data herein, the cardiac muscles show signs of swelling when the heart is removed from a human body. This means that when the heart is being transplanted, the heart only suffers from reversible damage and not the death of cardiac muscles. Therefore, cardiac damage caused by blood insufficiency (angina) and ischemia-reperfusion damage (organ transplant) is different in nature.

SUMMARY OF THE INVENTION

From the aforesaid biochemical processes of myocardial ischemia, it is clear to see that the release and activation of the enzymes is a crucial factor in causing the death of the cardiac muscles. As a result, it has been concluded that if there is a medicine able to chelate the calcium ions and render them not as readily available for activating the enzymes, or able to directly inhibit and break down the enzymes, the occurrence of dying cardiac muscles can be effectively lowered. From animal experiments, the inventor of the invention has inadvertently discovered that catechins can effectively reduce the death of myocardial cells in the animal subjects. However, more scientific research is still required to find out whether the phenomenon is induced by a catechol structure found in a part of the chemical structure of catechins, which can chelate calcium ions (the 2-hydroxy structure has been scientifically proven to be capable of chelating calcium), or because the mildly acidic catechol found in tea polyphenols is able to combine with and break down enzymes, which inhibits the enzymes' catalytic activities. In addition, the chelating effect of catechol may allow it to act like a calcium antagonist and lowers the calcium concentration within blood vessel cells, which in turn widens the blood vessels and lowers the afterload for the heart, subsequently reducing the cardiac work and preserving ATP for the heart, thereby alleviating angina. However, the exact concentration of catechol needed to achieve this is unclear.

A primary objective of the invention is to provide a pharmaceutical composition for the treatment and prophylaxis of a disorder and damage (such as angina and myocardial infarction) induced from myocardial ischemia, wherein the pharmaceutical composition comprises a compound of catechins.

More preferably, the pharmaceutical composition of the invention further comprises a medication for treating angina (such as nitrates or nitrites).

Figure 1:
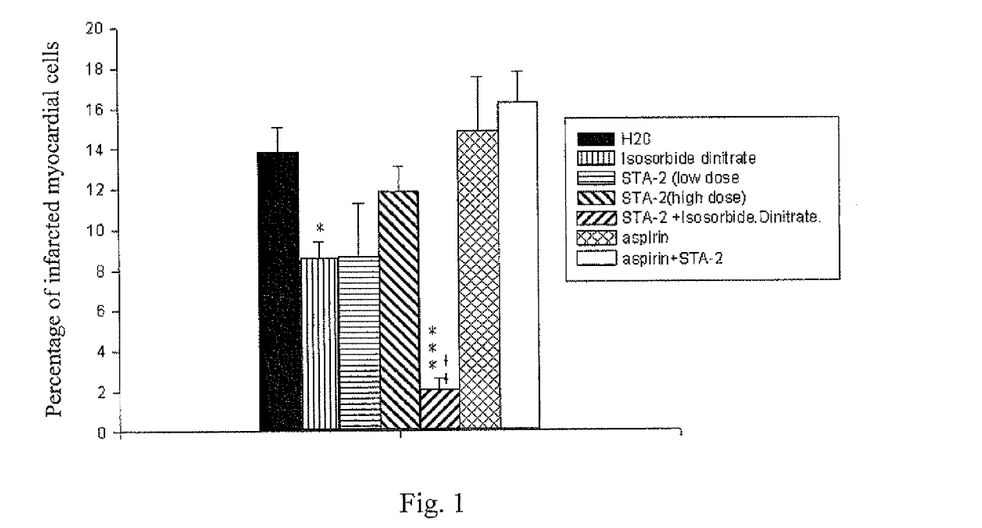
FIG. 1 is a graph that shows the effects of using STA-2 alone, or in combination with isosorbide dinitrate or Aspirin for treating infarcted myocardial cells resulted from partial myocardial ischemia.

In this invention, partial myocardial ischemia was simulated to induce the death of cardiac muscles (myocardial infarction) in animal experiments, which found that when tea polyphenol extracts (STA-2) comprising catechins and the nitrates-based antianginal drugs are used in combination, it showed significantly stronger inhibitive and protective effects against myocardial infarction as compared to using the nitrates-based drugs only (Embodiment 1, Table 1, and FIG. 1). Moreover, the results were also observed and confirmed in similar experiments repeated afterwards (Embodiment 2). Embodiment 2 is a preventive experiment in which catechins and nitrates were given to the tested animals before myocardial ischemia occurred instead of afterwards. The results indicated that the combination of catechins and the nitrates-based drugs can be used preventively against angina or myocardial infarction caused by myocardial ischemia.

The results from the invention showed that when only the nitrates-based drugs were used against myocardial infarction, it led to a 39% reduction in myocardial infarct size in comparison with those without drug treatment. Yet when catechins and the nitrates-based drugs were used in combination, the inhibitive effect it achieved against myocardial infarction was four times stronger than those treated with the nitrates-based drugs only, and the inhibitive effect was 46% higher than those treated with the nitrates-based drugs only, and 85% higher than those without drug treatment. (Embodiment 1 and FIG. 2) Such a significant difference in inhibitive effect against myocardial infarction indicates that a combination of tea polyphenol extract (STA-2) containing catechins with a nitrates-based drug would generate a synergistic effect, which remarkably enhances the inhibitive effect and protection function of the sole nitrates-base drug against myocardial infarction.

By using the model employing live animals to simulate cardiac muscle death induced from myocardial ischemia, the present invention has also disclosed that when a tea polyphenol extract (STA-2) containing catechins was applied at high dosage and low dosage separately, though STA-2 was found to be protective to cells and could reduce leaking of the intracellular lactate dehydrogenase (LDH) and creatinine phosphokinase (CPK), its effects on reducing and inhibiting the spread of myocardial infarction were insignificant. In the patent US2006/0116333A1 carried out by Japanese researchers, it had disclosed and proposed the use of polyphenols (including tea polyphenols) to protect cells from being damaged by free radicals during the transplant of hearts and brains back into live tissues, which is completely different from the cause of damage described herein; the damage described in US2006/0116333A1 is caused by free radicals, whereas in the present invention it is caused by energy insufficiency (ATP) and an elevation in calcium concentration.

The invention also provides a pharmaceutical composition in which tea polyphenol extracts (catechins) and nitrates-based antianginal medicines are used in combination, which has been shown to have significant effects on treating angina in the embodiment in which clinical trials on patients experiencing angina were carried out (Embodiment 3).

In the clinical trial, the tea polyphenol extracts (STA-2) comprising catechins and the nitrates-based medicine isosorbide dinitrate were used in combination, and the effects it achieved were compared to using isosorbide dinitrate or STA-2 alone. It was revealed that the tea polyphenol extracts (STA-2) comprising catechins used in combination with isosorbide dinitrate achieved an efficacy rate of 88.9% on reducing the occurrence of angina, reducing symptoms thereof, and inducing visible improvement on the electrocardiography (ECG), which was significantly higher than that of using only isosorbide dinitrate (68.9%) or the tea polyphenol extracts (STA-2) comprising catechins (56.7%).

In summary, both the animal experiments and the human clinical trial have indicated that the pharmaceutical composition comprising catechins and antianginal medicines described in this invention can be used for the treatment and prophylaxis of angina and following myocardial infarction induced from myocardial ischemia.

DETAILED DESCRIPTION OF PREFERRED EMBODIMENTS

The invention provides a pharmaceutical composition for the treatment and prophylaxis of a disorder induced from myocardial ischemia, which comprises a compound of catechins at an effective dose, wherein the disorder induced from myocardial ischemia is angina or myocardial infarction.

Preferably, the disorder induced from myocardial ischemia is angina.

Preferably, the disorder induced from myocardial ischemia is myocardial infarction.

Preferably, the pharmaceutical composition of the invention further comprises a medicine for treating angina.

Preferably, the medicine for treating angina may be nitrates, β-blockers, or calcium antagonists. More preferably, the medicine for treating angina may be nitrates or nitrites, such as amyl nitrite, erythrityl tetranitrate, glyceryl trinitrate, hexanitrate, isosorbide dinitrate, nitroglycerine, or pentaerythritol tetranitrate. Moreover, the medicine is preferably isosorbide dinitrate.

Preferably, the pharmaceutical composition of the invention further comprises Aspirin, and the disorder is unstable angina.

Preferably, the catechins are included in a tea polyphenol extract from tea leaves, and the pharmaceutical composition of the invention comprises the tea polyphenol extract.

Preferably, the tea polyphenol extract may be one or many types of catechins selected from the group consisting of EGCG, ECG, EGC, EC, GCG, CG, GC, and catechin. More preferably, the tea polyphenol extract includes more than 80 wt % of catechins. Most preferably, the tea polyphenol extract includes no less than 98 wt % of catechins.

Preferably, the tea polyphenol extract contains more than 60 wt % of EGCG.

The pharmaceutical composition of the invention may further comprise a diluent, an excipient, or a carrier.

The invention can be further understood by the use of following embodiments, whereas the embodiments are only explanatory and are not to be used to limit the scope of the invention in any ways.

All of the percentage and volume mentioned in the invention are based on weight unless indicated otherwise. Moreover, the sum of all of the mentioned percentage range is 100%.

Embodiment 1

Animal Experiments

The purpose of this embodiment is to investigate whether using the tea polyphenol extract comprising catechins alone (STA-2, XinNaoJian capsules, manufactured by Sinphar Tian-Li Pharmaceutical Co., Ltd.) could produce any protective effects against the death of myocardial cells induced from myocardial ischemia, and whether combining STA-2 and cardiovascular medicines in use could enhance the treating and prophylactic effects. STA-2 is extracted from tea leaves, and the catechins thereof occupy ≥98 (wt %) overall, wherein the EGCG therein takes up ≥60 wt %.

1. Observations on the death of myocardial cells: Animal experiments were done in order to simulate death induced from myocardial ischemia, in which the left descending branch from the coronary artery was ligated while the right descending branch was left intact, so as to induce partial ischemia and oxygen insufficiency to the myocardial cells. This was followed by releasing the left descending branch from the coronary artery from ligature to resume blood supply to the heart, and then the percentage of myocardial infarct size was calculated.
2. Biochemical analyses were carried out on: (1) creatinine phosphokinase (CPK) concentration; (2) lactate dehydrogenase (LDH) concentraion; and (3) nitric oxide (NO) concentraion.

Animals Used in the Experiments

The Crl:CD(SD) SPF rats were kept and fed in separate stainless steel cages, and the rats were less than 12 weeks old and weighed 350-450 g. The room temperature was controlled at 21±2° C., and the humidity at 30-70%; light/dark periods were alternated every 12 hours, and water and feeds (Purina Certified Rodent Chow, #001) for the rats were unlimited.

The Preparation of the Drug Solution and the Amount of Drug Administration

1. STA-2: Added the STA-2 powder into water to prepare 50 mg/ml (low dose) and 150 mg/ml (high dose) solutions.
2. Isosorbide dinitrate: Added isosorbide dinitrate (5 mg/tablet) into water to prepare a 3.75 mg/ml solution, and mixed it well before use.
3. Aspirin: Added 500 mg of Aspirin into water to formulate a 1.66 mg/ml solution.
4. STA-2+isosorbide dinitrate: Added the STA-2 powder and isosorbide dinitrate tablets into water to prepare a mixed solution with 50 mg/ml (low dose) of STA-2 and 3.75 mg/ml of isosorbide dinitrate.
5. STA-2+Aspirin: Added the STA-2 powder and Aspirin tablets into water to prepare a mixed solution with 50 mg/ml of STA-2 and 1.66 mg/ml of Aspirin.
6. The animals were divided into seven groups; with four rats in each group, and the rats were tube-fed with 5 ml/Kg of the aforesaid drugs once each day.

The Experimental Groups and Amount of Drug Administered

| Groups | Amount of drug administered |
|---|---|
| Group 1 (blank control group; water) | 0 |
| Group 2 (isosorbide dinitrate) | 18.75 mg/Kg |
| Group 3 (STA-2 (low dose)) | 250 mg/Kg |
| Group 4 (STA-2 (high dose)) | 750 mg/Kg |
| Group 5 (STA-2 (low dose) + isosorbide dinitrate) | 250 mg/Kg + 18.75 mg/Kg |
| Group 6 (Aspirin) | 8.3 mg/Kg |
| Group 7 (STA-2 (low dose) + Aspirin) | 250 mg/Kg + 8.3 .mg/Kg |

Method of Experiments

1. The seven groups of rats listed in the table above were fed with the medicine solutions at the amount of drug administered accordingly, and the feeding continued for seven days.
2. On the seventh day, the aforesaid seven groups of rats were subjected to ligature of the left descending branch from the coronary artery for one hour, before blood samples were taken therefrom for analysis.

(1) The rats were firstly anethesized by using ketamine and urethane before having their tracheas connected to a breathing machine.
(2) The rats were then connected to the ECG (electrocardiogram) machine. Subsequently, the rats' left thoracic cavities were cut in order to open the pericardial sac and have their electrocardiogram recorded.
(3) Ligated the left descending branch from the coronary artery with polyethylene suture (3/0).
(4) Delivered the medicine solutions via intraperitoneal (IP) injection at ⅓ the amount of drug administered used for tube-feeding.
(5) After 1-hour of ligature, the suture was cut in order to resume blood supply via the left descending branch from the coronary artery to the heart.
(6) After allowing the reperfusion to continue for 1 hour, approximately 5 c.c. of blood samples were taken from the left ventricle, followed by the excision of the heart for doing biopsies.

3. The heart was firstly cut into 5 slices and then stained with TTC at 37° C. Afterwards, the dyes were washed off by using a saline solution, and both sides of the specimens were photographed.
4. By using the Image Pro software, the surface area and the myocardial infarct size were calculated for both sides of the specimens.
5. The blood samples taken from the left ventricle were centrifuged to obtain serum samples therefrom, so as to analyze the concentrations of NO, LDH, and CPK therein.

Sample Analyses

1. The calculation of myocardial infarct size: after excising the hearts from the thoracic cavities of the rats, the hearts were placed on a platform and cut into 5 slices, with each of the slices of 2 mm in thickness. The 5 slices of a heart were stained with 2% TTC (2,3,5-Triphenyltetrazolium chloride) at 37° C. for one minute. The underlying principle of the staining is that dead myocardial cells would not be stained and would appear white in color, while the live cells could be stained and would appear to be red. After staining, both sides of the heart slices were photographed by using a digital camera with a standard ruler next to them. The photographed results were then uploaded into a computer and analyzed by using the Image Pro software, so as to calculate the myocardial infarct size and total surface area for each of the heart slices. Consequently, a percentage of myocardial infarction could be calculated for each of the hearts, by dividing a sum for the infarct size derived from both sides of the five heart slices with a sum for the total surface area therefrom, and then multiplied the resulted value by 100.
2. Analyzing the serum CPK, LDH, and NO concentrations: after taking blood samples from the left ventricles of the rats, the samples were centrifuged at 4° C., and the top-most layer of serum in each sample was separated from the rest and stored at −20° C. for future uses. (1) CPK and LDH concentrations: analyzed by using a serum biochemical analyzer; (2) NO concentration was analyzed by using a spectrophotometer kit.

Figure Analysis and Statistics

The serum CPK and LDH concentrations for the samples were presented in unit/ml, whereas the NO concentration was presented in $\mu M$. The rate of myocardial infarction was presented as a percentage. The figures were presented as average values (mean)±standard error of the mean (SEM).

Finally, p-value was derived from the results by using the t-test feature available in the Sigma Statis software. By comparing the p values from each group with the one from the blank control group (fed water only); if P<0.05, it represents a significant difference between the two compared groups, and is marked by a *. If P<0.01, it represents a very significant difference between the two, and is marked by . Finally, if P<0.001, it represents a most significant difference between the two, and is marked by *. When comparing the p values from the experimental groups with the drug control group (fed with isosorbide dinitrate only), the interpretation of the p values is identical as above, except that the * symbols are replaced with the + symbols.

Experimental Results

I. The treating effects of using STA-2 alone, or in combination with isosorbide dinitrate or Aspirin on infarcted myocardial cells induced from partial ischemia, as shown in Table 1 and FIG. 1.

TABLE 1

Comparison of myocardial infarction percentage between the experimental groups

| Groups | Myocardial Infarction Percentage (%) |
|---|---|
| Group 1 (blank control group: Water) | 13.81 ± 1.2 |
| Group 2 (isosorbide dinitrate) | 8.475 ± 0.93* |
| Group 3 (STA-2 (low dose)) | 8.6 ± 2.7 |
| Group 4 (STA-2 (high dose)) | 11.801 ± 1.3 |
| Group 5 (STA-2(low dose) + isosorbide dinitrate) | 2.04 ± 0.59***++ |
| Group 6 (Aspirin) | 14.75 ± 2.8 |
| Group 7 (STA-2 (low dose) + Aspirin) | 16.14 ± 1.7 |

When comparing the results with that of the blank control group,
*was used to indicate P < 0.05, and
***was used to indicate P < 0.001; while comparing the results with that of the positive control group (isosorbide dinitrate),
++was used to indicate P < 0.01.

Figure 2:
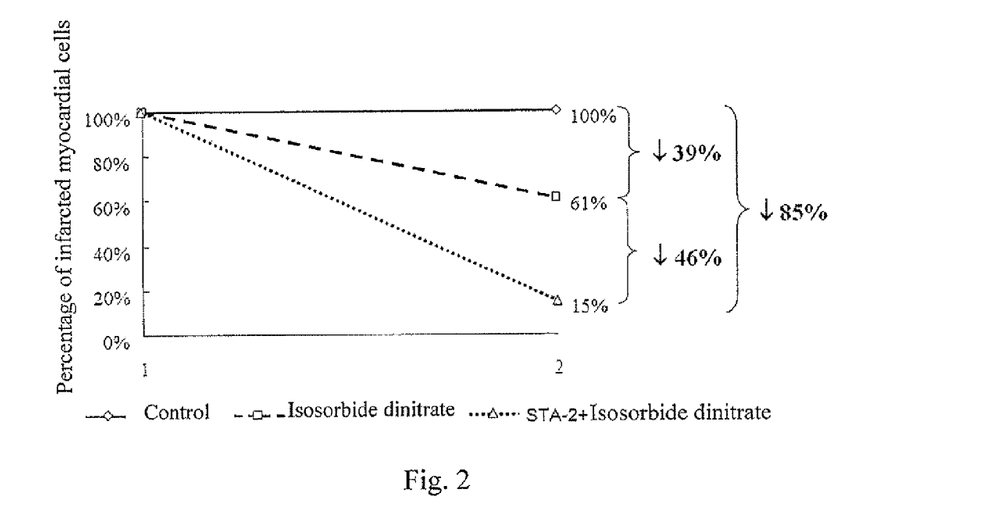
FIG. 2 is a graph that shows a comparison of relative percentage between the effects achieved in Group 1, Group 2, and Group 5 of experiments on inhibiting myocardial infarct size, according to the first embodiment of the invention.

Discussions on Table 1:
1. When isosorbide dinitrate was used alone, the comparison of its result with that of the blank control group showed that the p value was less than 0.05, which indicated a significant reduction in myocardial infarct size from the control group.
2. When STA-2 was used in combination with isosorbide dinitrate and compared with the blank control group, the p value was less than 0.001, which suggested that the combination of STA-2 and isosorbide dinitrate had significantly reduced the myocardial infarct size in test animals.
3. When STA-2 was used in combination with isosorbide dinitrate, as compared with using isosorbide dinitrate alone, it showed a compelling difference between the two (p<0.01). This shows the combination of STA-2 and isosorbide dinitrate could enhance the effects of isosorbide dinitrate on inhibiting the myocardial infarct size, and suggest STA-2 and isosorbide dinitrate could complement each other in regard to inhibiting myocardial infarct size.
4. On the other hand, the use of STA-2 alone in high dose or in low dose did not give rise to any statistical differences; while using Aspirin alone or using STA-2 combined with Aspirin did not produce any statistically meaningful effects, either.
5. It should be noted that in the animal experiments of the invention, the tested rats had only one of the coronary arteries ligated and the other one left intact, for the main purpose was to induce partial ischemia in the heart, in order to cause energy insufficiency and death of cardiac muscles subsequently. Consequently, long periods of ischemia resulted from stable angina (which is caused by restricted coronary artery) was induced in the rats, rather than unstable angina, which is the result of blood vessel damage leading to platelet aggregation and blood clots. Indirectly, the results also indicate the clinical use of Aspirin could assist the antianginal medicines in reducing clots formed by platelets, but could not help alleviate the death of myocardial cells caused by long periods of ischemia. Similarly, tea polyphenols could help prevent the release of biochemical enzymes like CPK and LDH from cardiac muscles into the blood, during the occurrence of ischemia (during organ transplant) and reperfusion (when an organ is transplanted into the human body) that give rise to free radicals and damaging the cell membrane. But just like Aspirin, the tea polyphenols could not help alleviate the death of myocardial cells caused by long periods of ischemia. Therefore, the results shown in Table 1 and FIG. 1 indicate that tea polyphenols must be used in combination with an antianginal medicine that reduces cardiac work for the heart (eg. the isosorbide dinitrate compound used in the experiments herein), to allow them to act against the death of myocardial cells caused by ischemia.
6. FIG. 2 is a graph that shows a comparison of relative percentage between the effects achieved in Group 1, Group 2, and Group 5 of experiments on inhibiting myocardial infarct size, according to this embodiment.

Discussions on FIG. 2:
1. According to FIG. 1, the percentage of myocardial infarct size of the blank control group (water) was designated as 100%, and then compared with that of the group using the combination of STA-2 and isosorbide dinitrate (Group 5), and the group using isosorbide dinitrate alone (Group 2), in order to compare their effects on inhibiting myocardial infarction.
2. The comparison showed that using isosorbide dinitrate alone to treat myocardial infarction achieved a 39% reduction in myocardial infarct size (relative to the untreated blank control group).
3. On the other hand, the combination of using STA-2 and isosorbide dinitrate to treat myocardial infarction achieved 85% reduction in myocardial infarct size (relative to the untreated blank control group).
4. The results suggested that in regard to treating myocardial infarction, the combination of STA-2 and isosorbide dinitrate was four times as effective as using isosorbide dinitrate alone; as the rate of myocardial infarction was 15% when treated with the combination of the medicine and STA-2, but was 61% when treated with the medicine alone.

Figure 3:
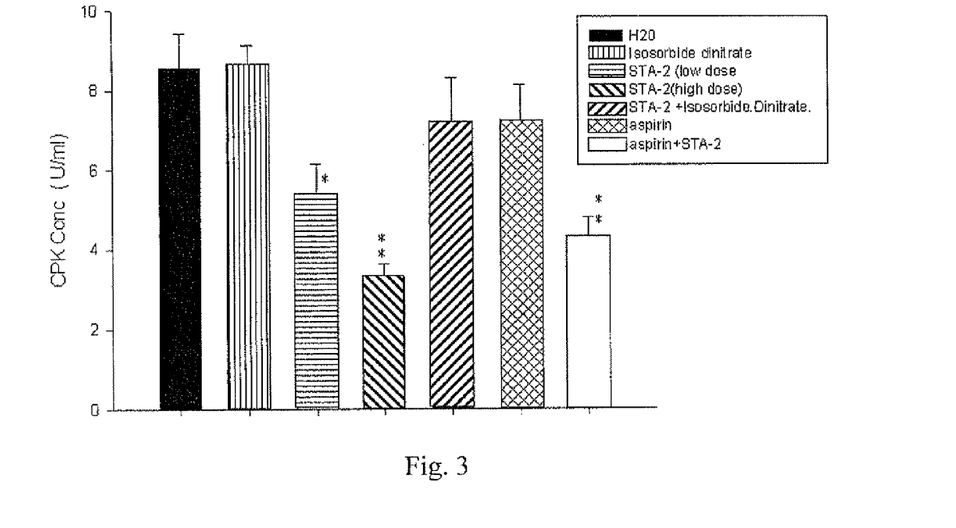
FIG. 3 is a graph that shows the effects of using STA-2 alone, or in combination with isosorbide dinitrate or Aspirin on serum CPK concentration in the case of infarcted myocardial animals resulted from ischemia.

Table 2 and FIG. 3 show the effects of using STA-2 alone or in combination with isosorbide dinitrate or Aspirin, on serum CPK concentration in animals with dying myocardial cells caused by ischemia.

TABLE 2

Comparison of serum CPK concentrations from the experimental groups

| Groups | Serum CPK concentration (unit/ml) |
|---|---|
| Group 1 (blank control group (water)) | 8.55 ± 0.89 |
| Group 2 (isosorbide dinitrate) | 8.63 ± 0.5 |
| Group 3 (STA-2 (low dose)) | 5.38 ± 0.79** |
| Group 4 (STA-2 (high dose)) | 3.13 ± 0.33*** |
| Group 5 (STA-2 (low dose) + isosorbide dinitrate) | 7.20 ± 1.12 |

TABLE 2-continued

Comparison of serum CPK concentrations
from the experimental groups

| Groups | Serum CPK concentration (unit/ml) |
|---|---|
| Group 6 (Aspirin) | 7.14 ± 1.00 |
| Group 7 (STA-2 (low dose) + Aspirin) | 4.29 ± 0.54** |

When comparing the results with that of the blank control group (water),
*was used to indicate $P < 0.05$,
**was used to indicate $P < 0.01$, and
***was used to indicate $P < 0.001$.

Discussions on Table 2/FIG. 3:
1. In FIG. 3, it could be observed that whether used in low dose or high dose, STA-2 was effective for lowering serum CPK concentration, and such effects are positively correlated to the dosage of STA-2.
2. When comparing the effects of using STA-2 and Aspirin together (Group 7) with that of the blank control group (water), a significant difference between the two group could be observed ($p<0.01$).

Figure 4:
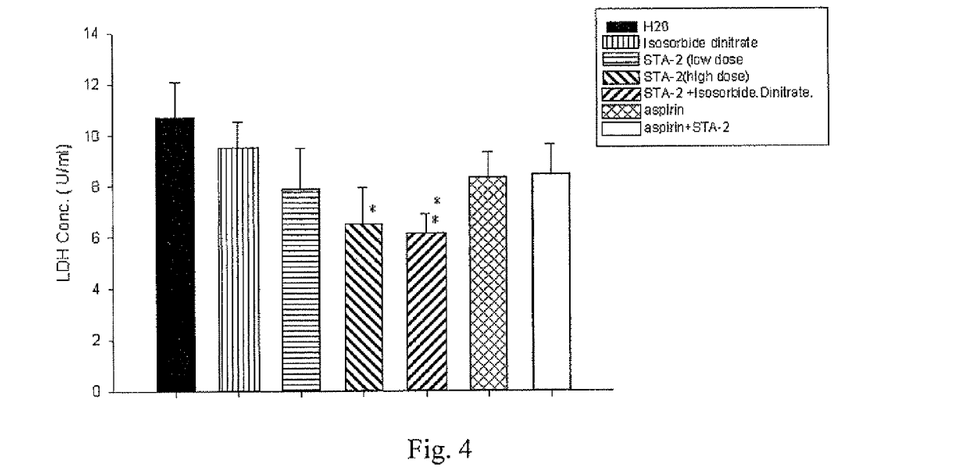
FIG. 4 is a graph that shows the effects of using STA-2 alone, or in combination with isosorbide dinitrate or Aspirin on serum LDH concentration in the case of infarcted myocardial animals resulted from ischemia.

III. Table 3 and FIG. 4 show the effects of using STA-2 alone or in combination with isosorbide dinitrate or Aspirin, on serum LDH concentration in animals with dying myocardial cells caused by ischemia.

TABLE 3

Comparison of serum LDH concentrations
from the experimental groups

| Groups | Serum LDH concentration (unit/ml) |
|---|---|
| Group 1 (blank control group (water)) | 10.72 ± 1.35 |
| Group 2 (isosorbide dinitrate) | 9.44 ± 1.06 |
| Group 3 (STA-2 (low dose)) | 7.88 ± 1.63 |
| Group 4 (STA-2 (high dose)) | 6.45 ± 1.49* |
| Group 5 (STA-2 (low dose) + isosorbide dinitrate) | 6.09 ± 0.81** |
| Group 6 (Aspirin) | 8.27 ± 1.05 |
| Group 7 (STA-2 (low dose) + Aspirin) | 8.43 ± 1.20 |

When comparing the results with that of the blank control group (water),
*was used to indicate $P < 0.05$, and
**was used to indicate $P < 0.01$.

Discussions on Table 3/FIG. 4:
1. In FIG. 4, is showed that using STA-2 at high dose (Group 4) alone was effective for lowering the LDH concentration, as compared with that of the blank control group (water).
2. When comparing the effects of using STA-2 (low dose) and isosorbide dinitrate in combination with the blank control group (water), a significant difference between the two groups could be observed ($p<0.01$).
3. Table 2 (FIG. 3) and Table 3 (FIG. 4) both indicated that a few intracellular biochemical enzymes (CPK and LDH) had been released into the bloodstream, which was the result of myocardial cell membrane damage, and such damage was likely to be caused by (1) the generation of free radicals induced from ischemia and then reperfusion, or (2) long periods of ischemia (but not caused by free radicals). The result (Table 2 and Table 3) serves as a proof that tea polyphenols could act as a free-radical antagonist, as disclosed in the patent US2006/0116333A1 (organ transplant—re-transplant into the human body). However, the result could not be used to indicate or deduce that whether being effective for antagonizing free radicals is equivalent to being effective for preventing cell death. As there is no positive relationships observed between the two, as indicated clearly in Table 1 (FIG. 1).

Figure 5:
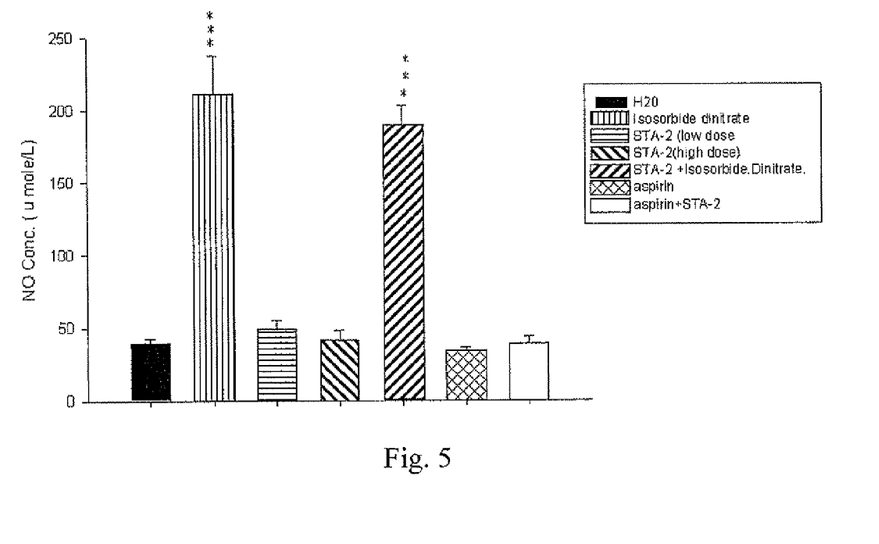
FIG. 5 is a graph that shows the effects of using STA-2 alone, or in combination with isosorbide dinitrate or Aspirin on serum NO concentration in the case of infarcted myocardial animals resulted from ischemia.

IV. Table 4 and FIG. 5 show the effects of using STA-2 alone or in combination with isosorbide dinitrate or Aspirin, on serum NO concentration in lab animals with myocardial cell damage induced from ischemia.

TABLE 4

Comparison of serum NO concentrations
from the experimental groups

| Groups | Serum NO concentration (μM) |
|---|---|
| Group 1 (blank control group (water)) | 39.38 ± 3.20 |
| Group 2 (isosorbide dinitrate) | 211.21 ± 26.00*** |
| Group 3 (STA-2 (low dose)) | 48.14 ± 6.70 |
| Group 4 (STA-2 (high dose)) | 40.79 ± 7.10 |
| Group 5 (STA-2(low dose) + isosorbide dinitrate) | 187.95 ± 15.83*** |
| Group 6 (Aspirin) | 33.2 ± 2.90 |
| Group 7 (STA-2 (low dose) + Aspirin) | 37.94 ± 5.80 |

When comparing the results with that of the blank control group (water),
***was used to indicate $P < 0.001$.

Discussions on Table 4/FIG. 5:
1. The result of NO concentration in FIG. 5 suggested that the mechanism isosorbide dinitrate reduces myocardial infarction is closely related to the generation of NO, and the underlying principle is that NO can reduce cardiac work for the heart, which allows the heart to retain more energy in the form of ATP.
2. When STA-2 was used alone, NO was not generated. But when STA-2 was used in combination with isosorbide dinitrate, a significant amount of NO was generated as a result. As a result, the aforesaid combination was more effective on inhibiting myocardial cell death than using isosorbide dinitrate alone (Group 2), which was resulted from actions of NO and STA-2 as well, though it is highly likely that STA-2 exerted its effects via another mechanism not related to NO. The mechanism of STA-2 still needs to be clarified by further scientific research in the future.

Embodiment 2

Animal Experiments

Prophylactic Experiment Against Myocardial Infarction

The aim of this embodiment is to investigate whether the combination of STA-2 extract and isosorbide dinitrate used in Embodiment 1 could provide any prophylactic actions against myocardial cell death induced from myocardial ischemia. The experimental steps in Embodiment 1 were repeated except for the step in which the medicines were delivered by intraperitoneal (IP) injection after the left descending branch from the coronary artery was ligated.

The percentage of myocardial infarction and serum NO concentration were illustrated in Tables 5 and 6, from which a consistent trend could be observed in this embodiment and Embodiment 1. In this embodiment, tea polyphenols and isosorbide dinitrate were not delivered via IP injection after ligating the left descending branch from the coronary artery, so as to observe if the percentage of myocardial infarction was lowered by treating the animals with the combination of medicines before ischemia (angina). Moreover, the results were demonstrated to be consistent with the ones shown in Tables 1 and 4, and suggested the combination of medicines was prophylactic against myocardial cell death. Therefore, it could be concluded that the combination of tea polyphenols with antianginal medicines was effective for treating and providing prophylactic actions against myocardial cell death induced from myocardial ischemia in the tested animals.

TABLE 5

Comparison of myocardial infarction percentage between the experimental groups

| Groups | Myocardial Infarction Percentage (%) |
|---|---|
| Group 1 (blank control group (water)) | 19.99 ± 1.90 |
| Group 2 (isosorbide dinitrate) | 12.19 ± 2.53* |
| Group 3 (STA-2 (low dose)) | 15.52 ± 1.29 |
| Group 5 (STA-2(low dose) + isosorbide dinitrate) | 7.43 ± 1.50** |

When comparing the results with that or the blank control group (water),
*was used to indicate P < 0.05 and a significant difference, and
**was used to indicate P < 0.01 and a very significant difference.

TABLE 6

Comparison of serum NO concentrations from the experimental groups

| Groups | Serum NO concentration (μM) |
|---|---|
| Group 1 (blank control group (water)) | 13.59 ± 1.04 |
| Group 2 (isosorbide dinitrate) | 96.86 ± 21.80*** |
| Group 3 (STA-2 (low dose)) | 13.38 ± 0.60 |
| Group 5 (STA-2 (low dose) + isosorbide dinitrate) | 71.97 ± 5.51*** |

When comparing the results with that of the blank control group (water),
***was used to indicate P < 0.001 and a most significant difference.

Embodiment 3

Human Clinical Trials

In this embodiment, a pharmaceutical composition comprising the combination of tea leave extract STA-2, which is mainly based on catechins, and isosorbide dinitrate, were used to treat human subjects. Results from the subjects were compared with that from the subjects treated with either isosorbide dinitrate or STA-2 only, in order to see if there is any differences in the occurrence of angina, the alleviation of symptoms, and improvement in ECG between the groups.
Experimental Data:
1. Grouping of subjects
Group A: Treated with the combination of catechin-comprising tea leave extract STA-2 and isosorbide dinitrate.
Positive control group A: Treated with isosorbide dinitrate only.
Group B: Treated with the catechin-comprising tea leave extract STA-2 only.
2. The standard for being classified as an angina sufferer:
Has symptoms that include brief chest pain (angina) induced from exercises or other circumstances that increase myocardial oxygen requirement; the symptoms occur more than twice a week, and the history of such symptoms has lasted for one month or more; said symptoms also lead to temporary lowering of S-T segment or changes in T waves in ECG 3. Information about the subjects
Group A: 45 people, 30 males, 15 females, aged between 50-75 years old.
Positive control group A: 45 people, 33 males, 12 females, aged between 52-78 years old.
Group B: 30 people, 12 males, 18 females, aged between 41-65 years old.
4. Method of treatment
Group A: isosorbide dinitrate 10 mg (t.i.d.)+catechin (STA-2) 200 mg (t.i.d.), which lasted for 8 weeks.
Positive control group A: isosorbide dinitrate 10 mg (t.i.d.), which lasted for 8 weeks.
Group B: Catechin (STA-2) 200 mg (t.i.d.), which lasted for 4 weeks.
5. The standard for evaluating effects of the treatment Valid:
The disappearance of angina and other major symptoms, with the ECG returned to normal.
Effective:
The lessening of angina and other major symptoms, with the ECG improved to following standards: the depression of S-T segment should be elevated for more than 0.05 mV after treatment, but short of the normal level; changes in the main T wave inversion should become shallower (more than 25%), or the T wave pattern should change from being flat to being elevated, and any improvements in the transmission blockage within the atria or ventricles of the heart.
Ineffective:
No improvements in angina and other major symptoms, with the ECG showing the same results as before the treatment.
Worsened:
With angina and other major symptoms become worse than before the treatment. The S-T segment of ECG is depressed for more than 0.05 mV than before the treatment, and the main T wave inversion becomes more pronounced (more than 25%), or the elevated T wave becomes flattened, and the flat T wave becomes inverted; or the subject experiences any ectopic rhythm or transmission blockage within the atria or ventricles of the heart.

Validity=number of valid cases÷total case number× 100;

Overall efficacy=(number of valid cases+number of effective cases)÷total case number×100;

Determination of effects from the treatment: If effects related to angina and other major symptoms is inconsistent with that of the ECG, the one with less effective result was deemed as the relevant result.
6. Results of the treatment

| Groups | Case number | Valid | Effective | Worsened | Ineffective | Validity (%) | Total validity (%) |
|---|---|---|---|---|---|---|---|
| Group A | 45 | 21 | 19 | 0 | 5 | 46.7 | 88.9 |
| Positive control group A | 45 | 16 | 15 | 0 | 14 | 35.6 | 68.9 |
| Group B | 30 | 6 | 11 | 0 | 13 | 20.0 | 56.7 |

The comparison between Group A and Positive control group A indicates a significant difference therebetween, p<0.05

What is claimed is:
1. A method of reducing myocardial cell death induced from myocardial infarction, wherein the method consists of administering to a subject in need thereof an effective amount of (i) a compound of catechins or a tea polyphenol extract from tea leaves, wherein the tea polyphenol extract comprises catechins comprising more than 60 wt % of EGCG, and (ii) an antianginal medicine selected from the group consisting of amyl nitrite, erythrityl tetranitrate, glyceryl trinitrate, hexanitrate, isosorbide dinitrate, nitroglycerine, and pentaerythritol tetranitrate, wherein the antianginal medicine is administered before, after or at the same time as administration of the compound of catechins or tea polyphenol extract.

2. The method of claim 1, wherein the disorder induced from myocardial ischemia is angina.

3. The method of claim 1, wherein the antianginal medicine is isosorbide dinitrate.

4. The method of claim 1, wherein the catechins are comprised in a tea polyphenol extract from tea leaves, and the polyphenol extract is administered to the subject instead of the compound of catechins.

5. The method of claim 4, wherein the tea polyphenol extract comprises one or more catechins selected from the group consisting of epicatechin (EC), epigallocatechin (EGC), epicatechin gallate (ECG), epigallocatechin gallate (EGCG), gallocatechin-3-gallate (GCG), gallocatechin (GC), catechin-3-gallate (CG), and catechin.

6. The method of claim 5, wherein the tea polyphenol extract is composed of more than 80 wt % of catechins.

7. The method of claim 6, wherein the tea polyphenol extract is composed of no less than 98 wt % of catechins.

8. The method of claim 4, wherein the disorder induced from myocardial ischemia is angina.

* * * * *